United States Patent [19]
Banayan

[11] Patent Number: 5,858,795
[45] Date of Patent: Jan. 12, 1999

[54] METHOD FOR DETERMINING THE PERCENT FAT OF A MEAT PRODUCT

[76] Inventor: Daniel Banayan, P.O. Box 261338, Encino, Calif. 91426

[21] Appl. No.: 893,590

[22] Filed: Jul. 14, 1997

[51] Int. Cl.[6] ..................................................... G01N 5/04
[52] U.S. Cl. ................................. 436/71; 73/76; 436/155; 426/240
[58] Field of Search ................................. 422/78; 436/21, 436/71, 155; 73/73, 76; 426/240

[56] References Cited

U.S. PATENT DOCUMENTS

| | | | |
|---|---|---|---|
| 3,673,852 | 7/1972 | Davis | 73/76 |
| 3,890,825 | 6/1975 | Davis | 73/76 |
| 4,398,835 | 8/1983 | Athey et al. | 374/17 |
| 4,753,889 | 6/1988 | Collins | 436/23 |

*Primary Examiner*—Lyle A. Alexander
*Attorney, Agent, or Firm*—Albert O. Cota

[57] ABSTRACT

A device (10) for determining the percent fat of a meat product such as beef or pork. The device 10 is presented in two designs, the first design uses a mechanical device in the form of a slide chart (12) and the second design employs an electronic device which is disclosed in three design configurations. The slide chart includes a stationary member (14) having a plurality of percent moisture windows (30) and percent fat windows (32) and a movable member (62) having a multiplicity of percent moisture figures (72) and percent fat figures (74). When a selected percent moisture figure (72) is located on the percent moisture window (30) the equivalent percent fat figure (74) is displayed on the percent fat window (32). The first design of the electronic device consists of a hand-held electronic calculator (90) which calculates the percent fat of the meat product when the percent moisture is known. The second design of the electronic device utilizes a percent moisture analyzer (110) that is connected, via a cable assembly (119), to an electronic calculator (94) which calculates the percent fat. The third electronic device design consists of an integrated percent moisture and fat analyzer (108).

2 Claims, 6 Drawing Sheets

METHOD FOR DETERMINING THE PERCENT FAT OF A MEAT PRODUCT

TECHNICAL FIELD

The invention pertains to the general field of percent fat analyzers for meat products. More particularly, the invention discloses a mechanical device and three electronic devices that can be used to analyze and calculate the percent fat of a meat product such as beef and pork.

BACKGROUND ART

For many years the attitude of living healthy has become a primary concern of both men and women of all age groups. The need for exercise and healthy eating is now a way of life for a great majority of People.

To assist in maintaining a healthy lifestyle, many new products and concepts have been introduced. These can range from membership gyms and home exercise equipment to special foods and recipes for health-conscious eating. One of the primary concerns of the health-food industry is the ability to disclose to the consumer the nutrition information for a specific food. Most healthy-conscious individuals are very interested in the amount of calories, sodium and, especially fat that is present in the food they eat.

This information is especially helpful in meats such as beef and pork, which typically have a high percentage of fat. The determination of the percent fat in beef and pork currently requires considerable time and effort to produce accurate results due to the equipment needed to calculate the fat content. Obviously, if a device is available that is capable of quickly and accurately measuring the percent fat of beef and pork, it would greatly assist in the continuing maintenance of healthy-conscious individuals.

A search of the prior art did not disclose any patents that read directly on the claims of the instant invention, however the following U.S. patents are considered related:

| U.S. Pat. No. | INVENTOR | ISSUED |
| --- | --- | --- |
| 4,753,889 | Collins | 28 June 1988 |
| 3,909,598 | Collins, et al | 30 September 1975 |

The 4,753,889 patent discloses a method and an apparatus for quantitatively measuring solids. The apparatus provides rapid and accurate determinations using microwave heating, electronic balance weighing and solvent extracting of solubles. The method involves subjecting a weighed sample to microwave drying for a preselected time, reweighing to obtain the dry weight and determine volatile loss, solvent extracting the dried sample to determine fats, oils and other extractables followed by final measurement of residual solids. The apparatus sequentially actuates the required weighing, microwave heating, solvent extraction, redrying, reweighing and calculation of the percentages of volatiles, solvent solubles and solids.

The 3,909,598 patent discloses an apparatus and method for automatically determining weight changes in substances containing volatile material. The apparatus automatically determines the percentage of volatiles in a substance which contains unknown quantities of moisture and the like. A digital panel meter provides a readout coupled with the ability to recall the original weight and the weight obtained after removal of the volatile material.

DISCLOSURE OF THE INVENTION

The invention discloses a device for determining the percent fat of a meat product.

In its most basic design, the device consists of:

a) means for determining the percent moisture of the meat product, b) means for entering the Percent moisture into the device, and c) means for reading on the device the percent fat equivalent to the entered percent moisture.

The device is primarily designed to determine the percent fat of either beef or pork. However, the percent fat of other meat products such as ostrich, buffalo, venison, etc., can also be determined.

In order to use the device, it is first necessary to determine the moisture content of the meat product. This is determined by performing a series of steps which include: weighing a sample of a wet preheated meat product to obtain a wet weight, subjecting the preheated meat product to a heat source to allow volatile solubles to be extracted, applying the heat source until the meat product is substantially dry and finally reweighing the meat product to obtain the dry weight. The dry weight is subtracted from the wet weight and the remainder is divided by the wet weight. The resulting quotient is then multiplied by one-hundred to obtain the percent moisture of the meat product. The above steps can be performed manually or automatically as described below.

The device is disclosed in two design configurations. The first design utilizes a mechanical design in the form of a slide chart. On one side of the slide chart the percent fat of beef is shown while on the reverse side the percent fat of pork is shown. The second design employs an electronic device which is disclosed in three design configurations. The first design consists of a small, portable electronic calculator that is dedicated to calculating the Percent fat of either beef or pork when the percent moisture of the meat product is known and entered into the calculator. The second design utilizes in combination a percent moisture analyzer that is connected through a cable assembly to an electronic calculator which calculates the percent fat of the meat product. The third electronic design Is an integrated percent moisture and fat analyzer that encompasses within a single enclosure all the elements to determine the percent moisture and fat content of a meat product.

In view of the above disclosure, it is the primary object of the invention to provide an easily operated device which can quickly determine the percent fat of a beef or pork product.

In addition to the primary object, it is also an object of the invention to provide a device that:

requires no manual entries in the second and third designs of the electronic devices, requires no learning skill to operate, is portable, is reliable, is easily readable, is cost effective for both small size meat markets and large meat processors.

These and other objects and advantages of the present invention will become apparent from the subsequent detailed description of the preferred embodiment and the appended claims taken in conjunction with the accompanying drawings.

BEST MODE FOR CARRYING OUT THE INVENTION

The best mode for carrying out the invention is presented in terms of a preferred embodiment that is disclosed in two designs as shown in FIGS. 1–10. The first design employs a mechanical calculating device and in the second design an electronic calculating device is used which is further disclosed in three design configurations. In both the mechanical and electronic designs, the percent fat of a meat product, such as beef or pork, can be determined by first determining the percent moisture of the meat product.

The percent moisture of the beef or pork product is determined by performing the following steps:

a) weigh a sample of a preheated meat product to obtain the wet weight, b) subject the preheated meat product to a heat source which may be produced by either hot air provided by a convection oven, or infrared radiation provided by heat lamps or quartz heaters. Apply the heat until the meat product is substantially dry, c) remove the meat product from the heat source and reweigh it to obtain the dry weight, d) calculate the percent moisture of the meat product by solving the following equation:

$$\text{percent moisture} = \frac{\text{wet weight} - \text{dry weight}}{\text{wet weight}} \times 100$$

Figure 1:
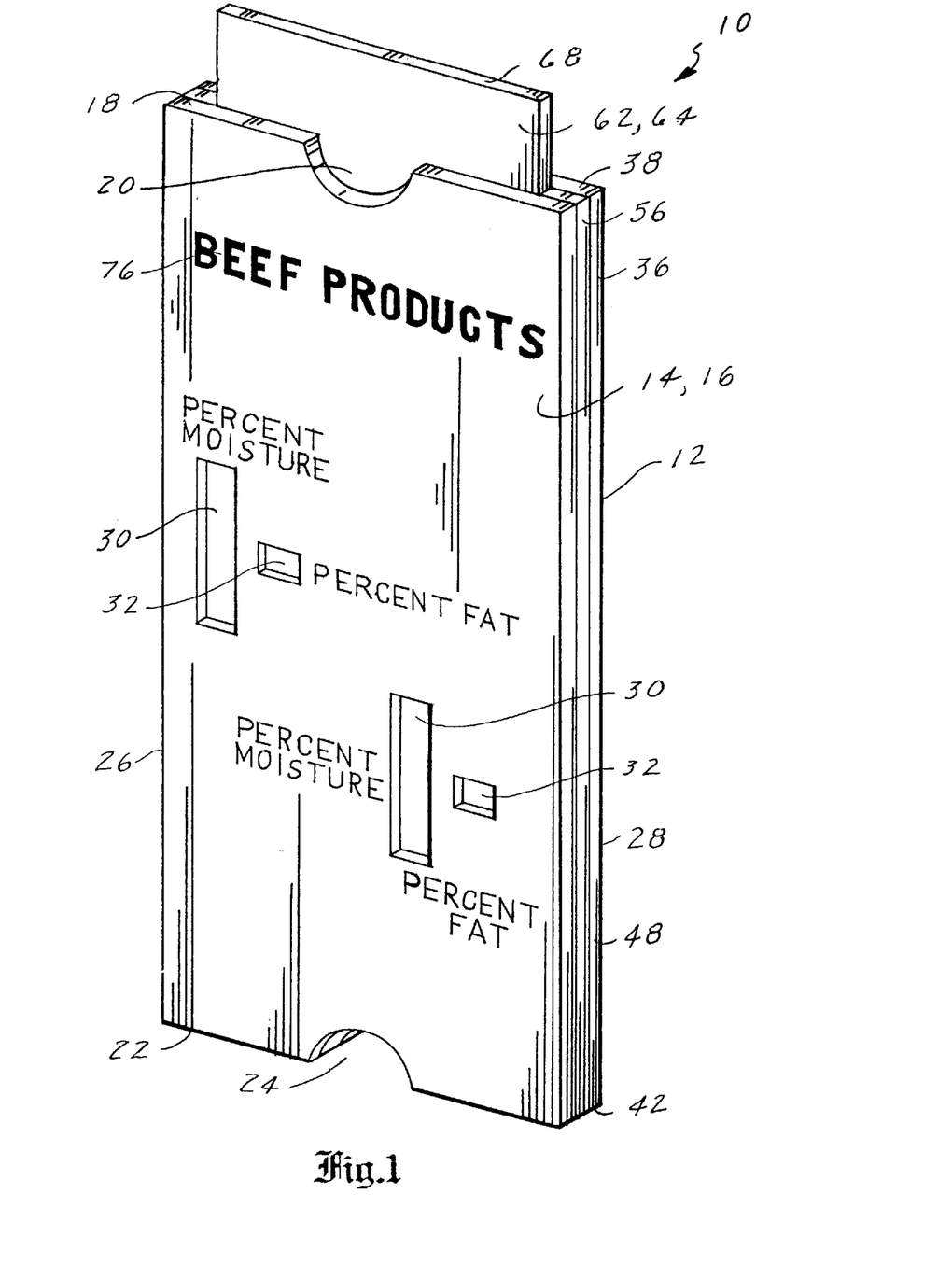
FIG. 1 is a perspective view of a slide chart shown with a stationary member and a movable member partly extracted.

The mechanical calculating device of the preferred embodiment, is comprised of a slide chart 12, as shown in FIG. 1, that is further comprised of two major elements: a stationary member 14 and a movable member 62.

The stationary member 14 is comprised of a front section 16 and a back section 36.

Figure 2:
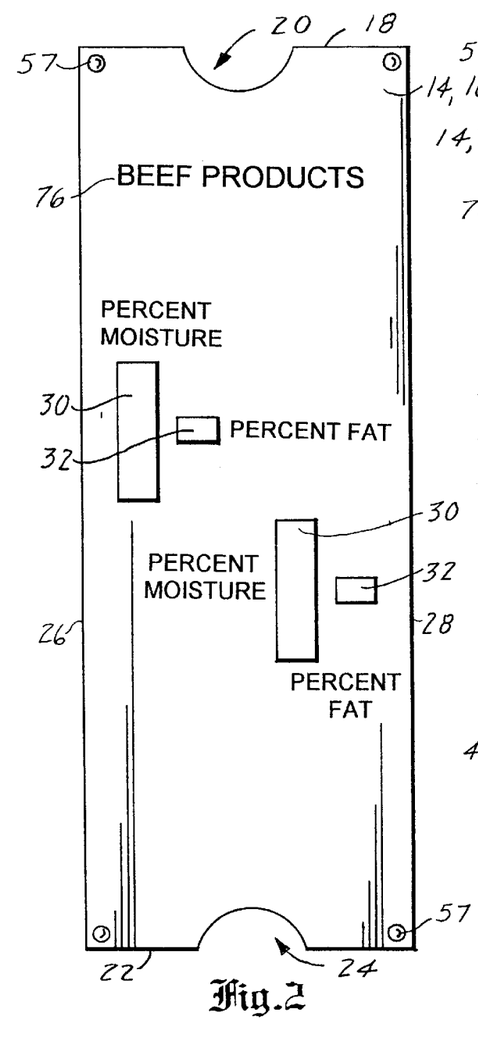
FIG. 2 is an elevational view of the front section of the slide chart.

The front section 16, as best shown in FIG. 2, includes an upper edge 18 having a substantially centered finger opening 20, a lower edge 22, also having a substantially centered finger opening 24, a left edge 26 and a right edge 28. On the front section 16 is located at least one, but preferably a plurality of, percent moisture window(s) 30. Adjacent to the percent moisture window(s) 30 is located at least one, but preferably a like plurality of, percent fat window(s) 32.

Figure 3:
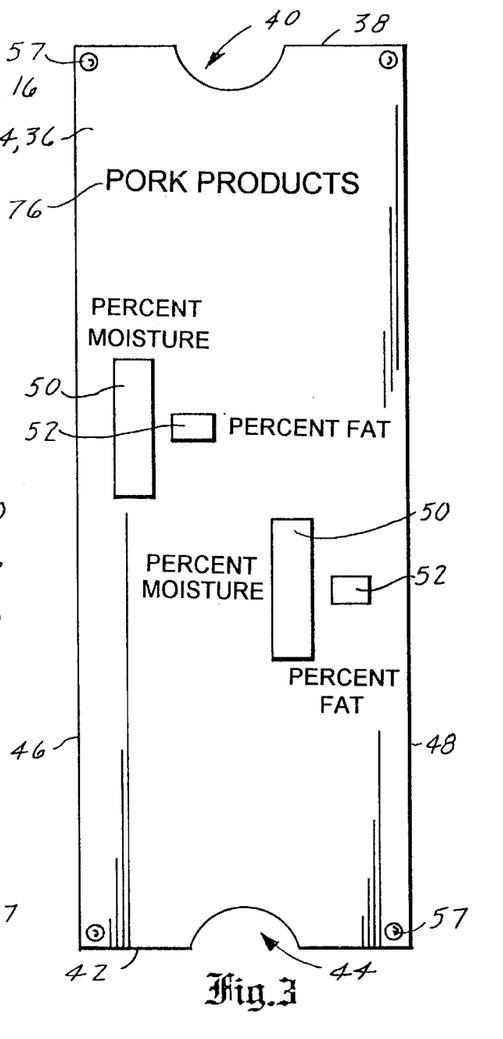
FIG. 3 is an elevational view of the back section of the slide chart.

The back section 36, as shown in FIG. 3, has similar dimensions as the front section 16 and also includes an upper edge 38 having a substantially centered finger opening 40, a lower edge 42, also having a substantially centered finger opening 44, a left edge 46 and a right edge 48. On the back section 36 is located at least one, but preferably a plurality of, percent moisture window(s) 50. Adjacent to the percent moisture window(s) 50 is located at least one, but preferably a like plurality of, percent fat window(s) 52.

Figure 4:
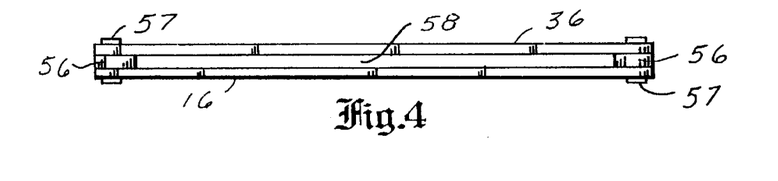
FIG. 4 is an end view of the stationary section showing the location of the narrow spacers which allow a slot to be formed that receives the movable member.

Along the left edges 26,46 and the right edges 28,48 of the front and back sections 16,36 is fitted a narrow spacer 56 as shown in FIG. 4. When the spacers 56 are attached, by a plurality of fasteners i.e., rivets, the front and back sections form a longitudinal slot 58 therethrough.

Figure 5:
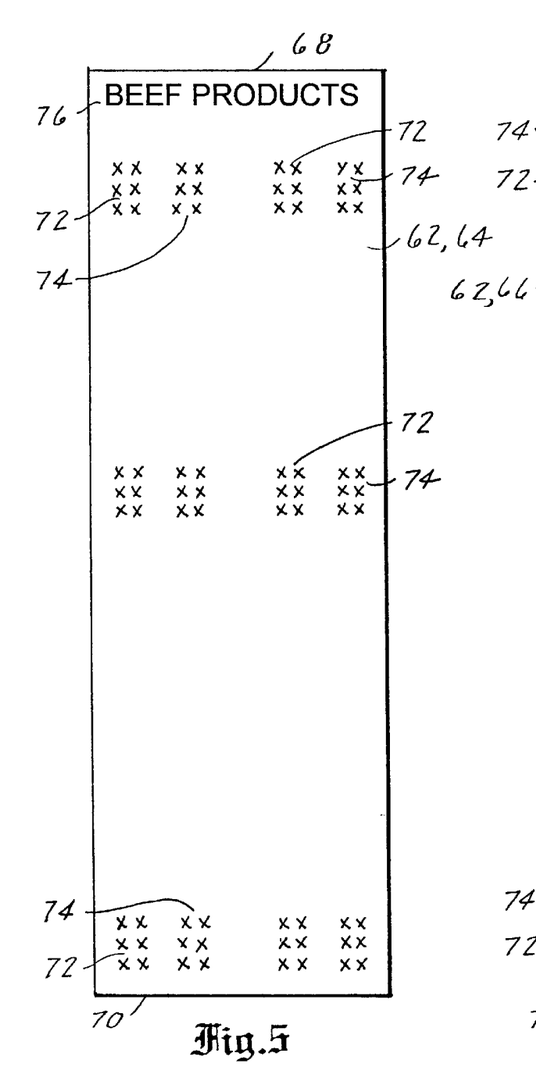
FIG. 5 is an elevational view of the front side of the movable member.
Figure 6:
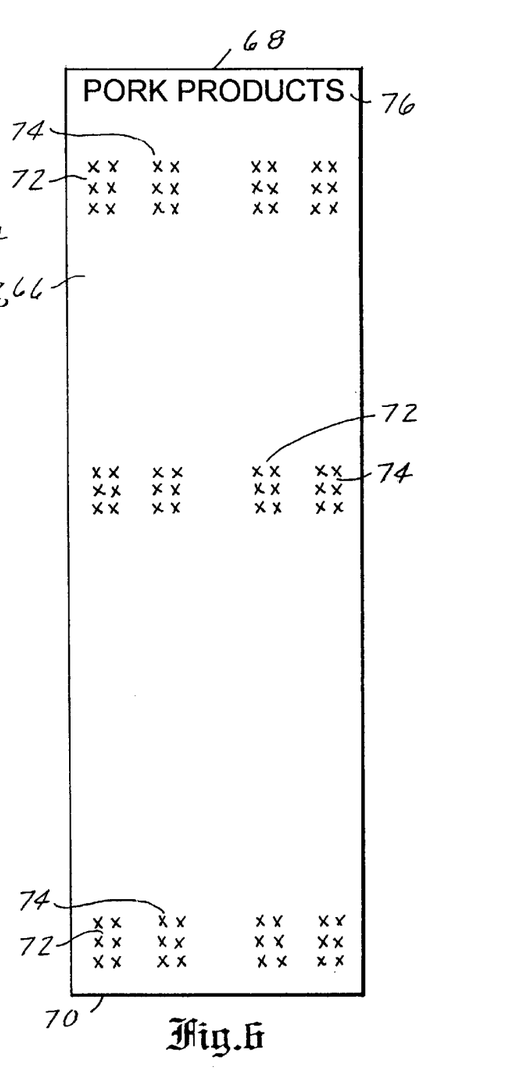
FIG. 6 is an elevational view of the back side of the movable member.

The movable member 62, as shown in FIGS. 5 and 6, includes a front side 64, a back side 66, an upper edge 68 and a lower edge 70. The movable member 62 as shown in FIG. 1, is dimensioned to traverse through the longitudinal slot 58 on the stationary member 14. The movable member 62 includes at least one row that displays a multiplicity of percent moisture figures 72 that are in alignment with the percent moisture window 30; and at least one row that displays a multiplicity of equivalent percent fat figures 74 that are in alignment with the percent fat window 32 on the front and back sections 16,36.

In the preferred embodiment, the front section 16 of the stationary member displays a first meat product i.e., a beef product and the back section 36 displays a second meat product i.e., a pork product. Likewise, the movable member 62 is produced to include beef figures on one side and pork figures on the reverse side.

To utilize the slide chart 12, the type of meat product is selected by referring to the key word 76 on the front of the slide chart 12 as shown in FIGS. 2 and 3. The upper or lower edge 68,70 of the movable member is grasped along the centered finger openings 20,24 or 24,44 located respectively on the front and back sections 16,36. The movable member 62 is then moved up or down along the longitudinal slot 58 until a selected percent moisture figure is displayed on the percent moisture window 30. Upon this occurrence, the percent fat figure equivalent to the selected percent moisture figure is displayed on the percent fat window 32.

Figure 7:
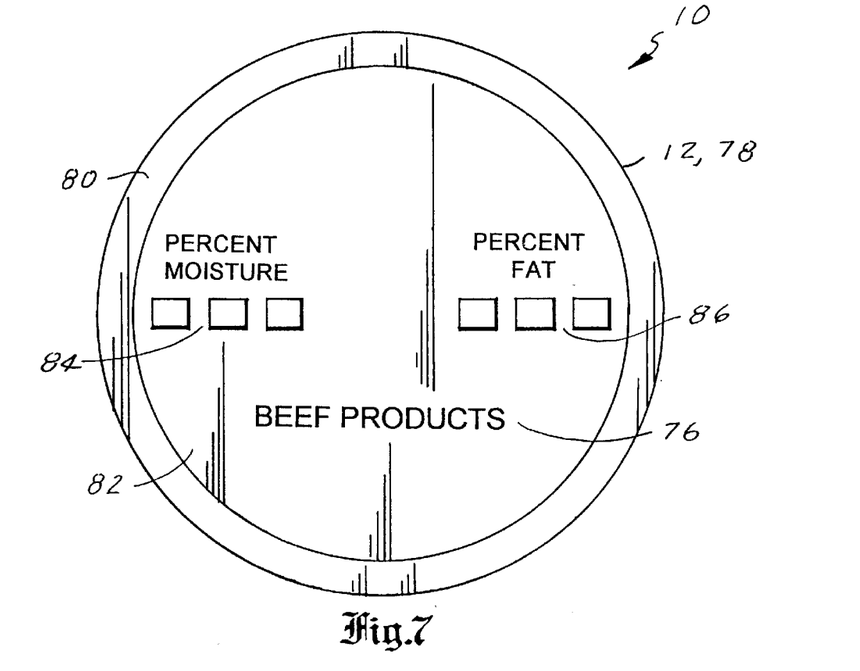
FIG. 7 is an elevational view of a circular slide chart.

The slide chart 12 may have a rectangular shape as shown in FIGS. 1–6, or the slide chart may be configured in a circular shape 78 as shown in FIG. 7. In the circular slide chart 12 two wheels are employed: a stationary outer wheel 80 and a rotatable inner wheel 82. On one side of the slide chart 12 are located the figures pertaining to beef products and on the reverse side the figures pertaining to pork products are shown. Near the edge of the outer wheel 80 are located the percent moisture figures and near the opposite edge are located the equivalent percent fat figures.

To use the circular slide chart 12, the inner wheel is rotated until a selected percent moisture figure of the beef or pork is displayed on a percent moisture window 84 located near the edge of the inner wheel 82. Near the opposite edge of the inner wheel 86 is located a percent fat window 86 where the equivalent percent fat of the beef or pork is displayed.

Figure 8:
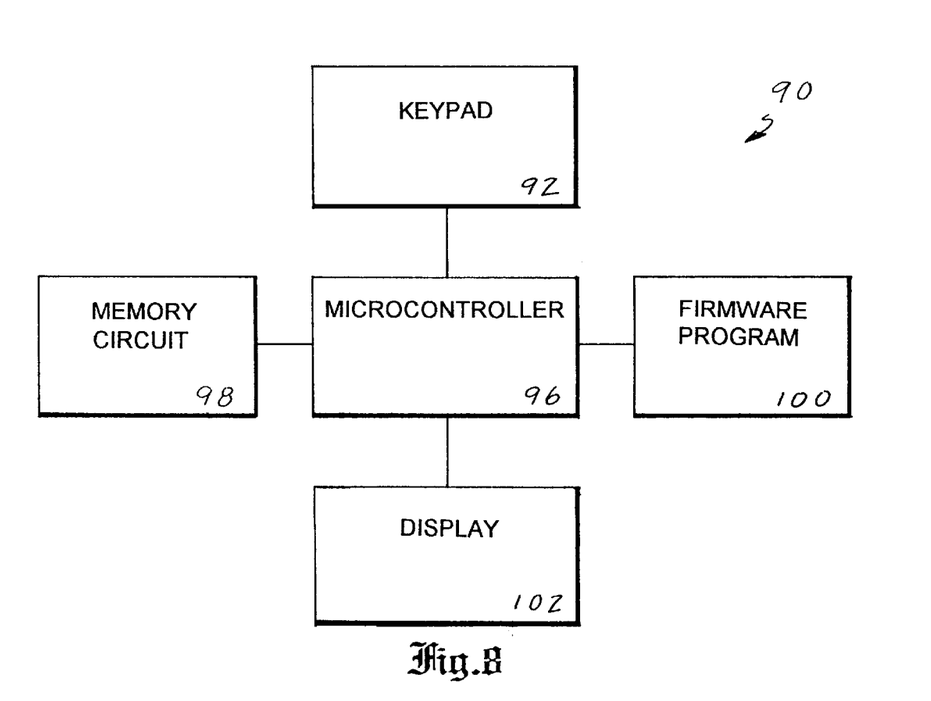
FIG. 8 is a block diagram of an electronic calculator that calculates the percent fat of a meat product when the percent moisture of the meat product is applied to the calculator via a keypad.

The first design configuration of the electronic calculating device, utilizes an electronic calculator 90, as shown in FIG. 8, which is comprised of the following major elements: a keypad 92, a microcontroller 96, and a display 102.

The keypad 92 includes a "B" key and a "P" key. The "B" key is pressed when calculating the percent fat of a beef product and the "P" key is pressed when calculating the percent fat of a pork product. The keypad also includes ten keys ranging from 0–9. These keys are used to enter the percent moisture of either the beef or pork products. The two methods for determining the percent moisture are described supra. Preferably the keypad 92 is comprised of a matrix keypad that supports at least twelve keys using a total of seven lines which are applied to the microcontroller 96 as shown in FIG. 8. The microcontroller 96 includes a register or memory 98 and a firmware program 100.

The memory 98 includes circuit means for receiving and storing the percent moisture figure of the beef or pork product. This figure is received by the memory 98 when the figure is entered into the ten keys on the keypad 92. When entering the percent moisture figure it is not necessary to enter a decimal point, as this point is automatically entered by the firmware program.

There are many types of microcontrollers 96 that can be used to operate the device 10. One such design which is manufactured by Holtek®, integrally incorporates a keypad decoder and display driver. By using this type of integrated microcontroller the number of parts needed, and the space requirements (size of Pa board) are reduced as well as reducing the overall cost of the electronic calculator 90.

The firmware program 100© which was developed by and copyrighted by the Applicant becomes operational when an ON-OFF switch on the calculator is turned ON wherein the switch also functions as a reset switch. After the calculator is ON, either the "B" key or the "P" key is 5 depressed which allows the firmware program 100© to solve the following beef formula or pork formula:

$$\text{percent fat of beef} = \frac{77.4 - \text{percent moisture of beef}}{0.786}$$

$$\text{percent fat of pork} = \frac{78.4 - \text{percent moisture of pork}}{0.787}$$

When either of the two formulas is solved, the percent fat of either the beef or the pork is determined and shown on the display 102.

The display 102 as also shown in FIG. 8, includes a means for receiving the output from the microcontroller 96 and displaying the percent fat of the beef or pork meat products. The display may utilize a light emitting diode (LED) or a display that is comprised of a liquid crystal display (LCD). Additionally, the display 102 is preferably comprised of an alpha-numeric display that includes the letter "B" or "P" which precedes or follows the beef or pork percent fat figures. The letters are controlled by the firmware program 100©, thus, input errors are precluded or at least minimized by viewing the display and confirming that a beef or pork product is being analyzed.

Figure 9:
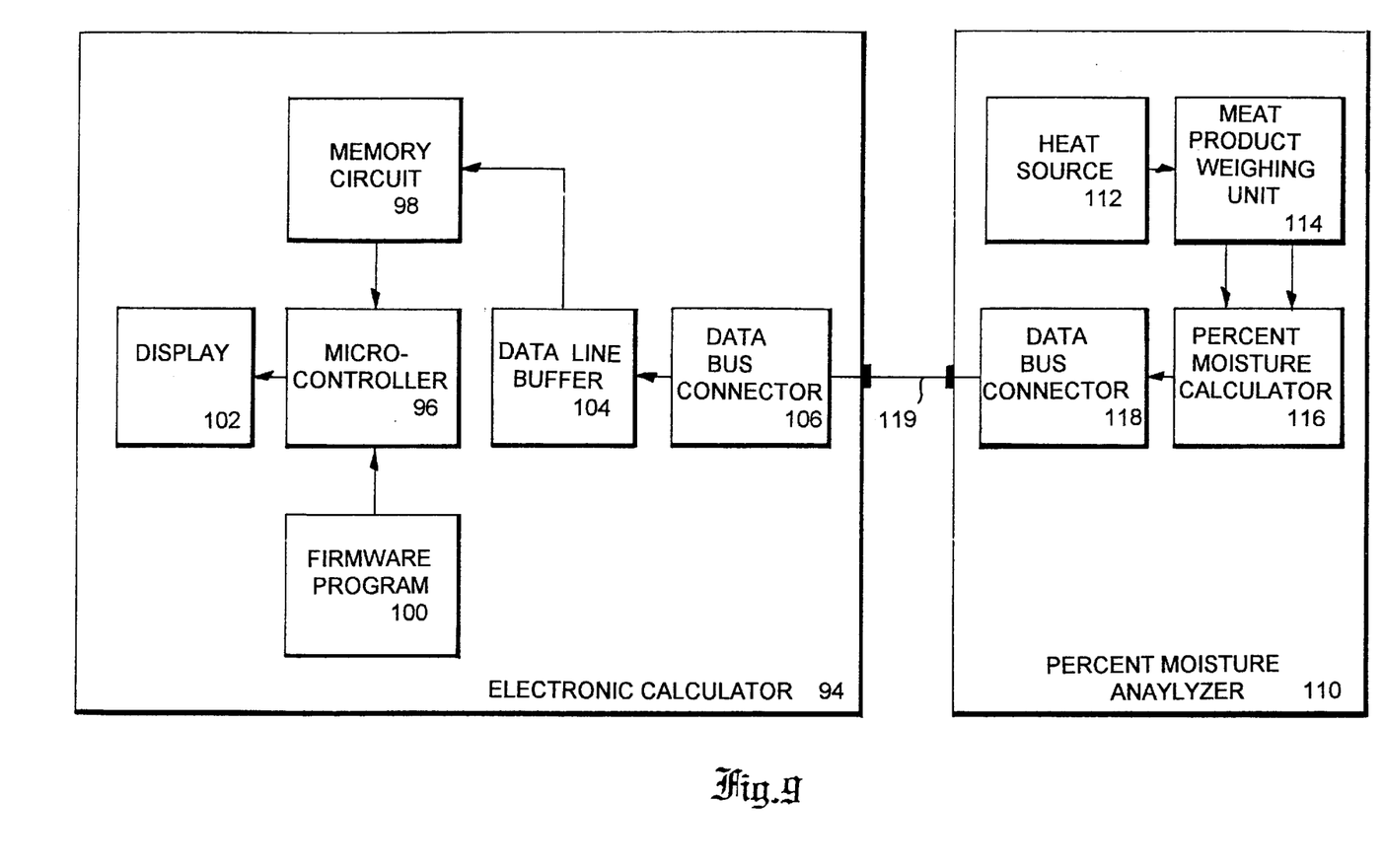
FIG. 9 is a block diagram of an electronic percent moisture analyzer that is directly connected to a separate electronic calculator which displays the percent fat of a meat product.

The second design configuration of the electronic calculating device utilizes an electronic calculator 94 and a separate percent moisture analyzer 110 as shown in FIG. 9.

The electronic calculator 94 is comprised of the following major elements: a microcontroller 96, a memory circuit 98, a firmware program 100©, a display 102, a data line buffer 104 and a data bus connector 106. The percent moisture analyzer 110 is comprised of the following major elements: a heat source 112, a meat product weighing unit 114, a percent moisture calculator 116 and a data bus connector 118.

The meat product weighing unit 114 has means, such as a tray, for supporting a quantity of a wet preheated beef or pork product. The unit 114 also has means for initially determining the weight of the wet preheated beef or pork product and the weight of the beef or pork product after the product has been substantially dried by the heat source 112 as described supra. From the meat product weighing unit 114 the wet and dry weight of the meat product is applied to the percent moisture calculator 116. The calculator includes means for calculating the percent moisture of the beef or pork product from the wet and dry weight data supplied by the meat product weighing unit.

The percent moisture of the beef or pork product is applied to the input of the data bus connector 118 which has an output that is connected to the input of the data bus connector 106, located in the electronic calculator 94, via a cable assembly 119. The cable assembly 119 is typically equipped with RS232 connectors which are inserted into RS232 receptacles located on the data bus connector 106 and 118.

From the data bus connector 106, which is located in the electronic calculator 94, the percent moisture data is applied through a data line buffer 104 to a register or memory circuit 98 which has means for receiving and storing the percent moisture of the beef or pork product. The memory circuit 98 and firmware program 100 are elements of the microcontroller 96 as shown in FIG. 9. The firmware program 100© is designed to solve a beef formula or a pork formula, as described supra, which provides the equivalent percent fat of the beef or pork product being analyzed. From the microcontroller 96 is also connected a display 102 as also shown in FIG. 9. The display includes a means for receiving and displaying the percent fat of the beef or pork product.

Figure 10:
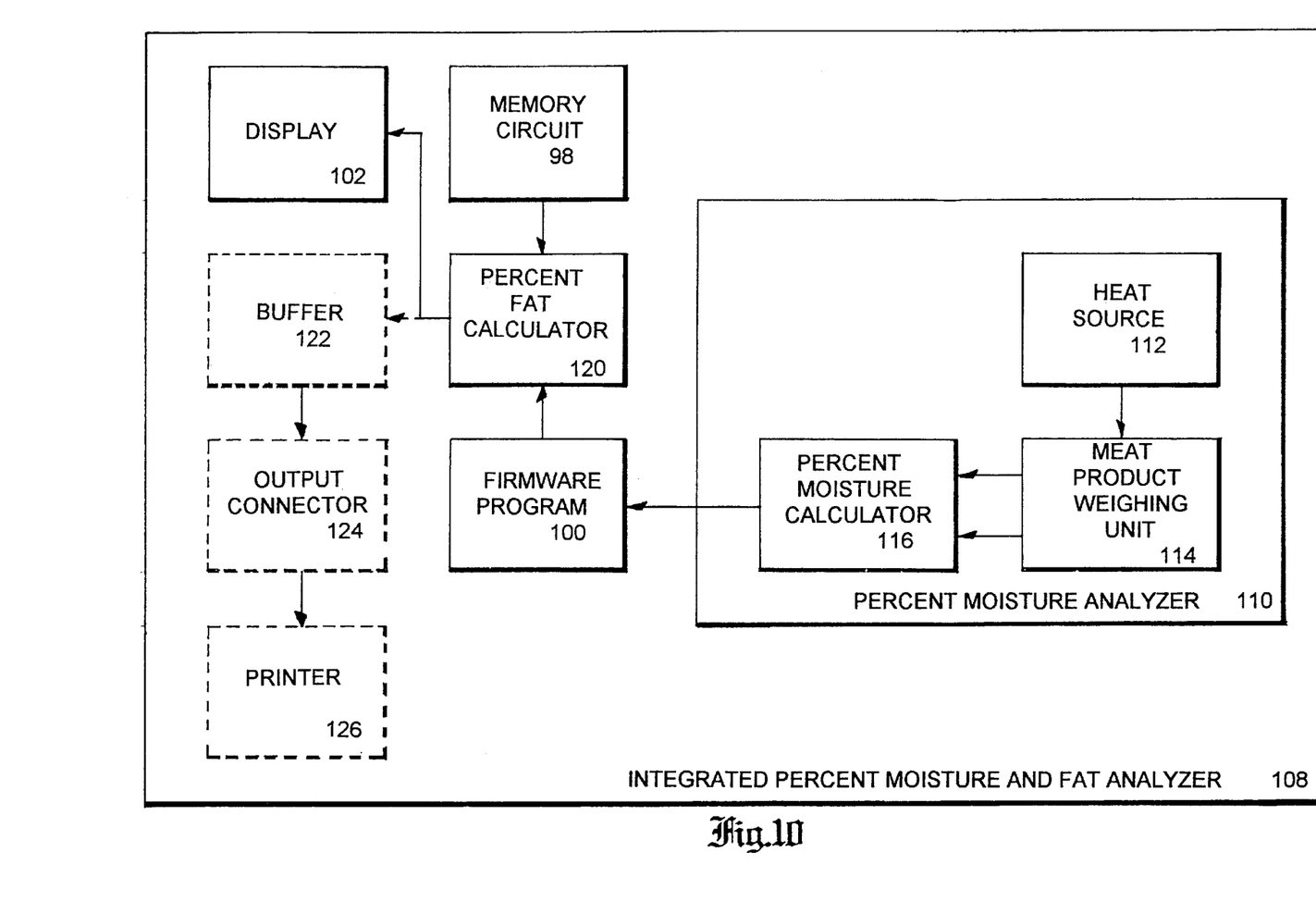
FIG. 10 is a block diagram of an integrated percent moisture and fat analyzer.

The third design configuration of the electronic calculating device is an integrated percent moisture and fat analyzer 108 as shown in FIG. 10. The integrated analyzer 108 is comprised of the following major elements: a percent moisture analyzer 110 which is further comprised of a heat source 112, a meat product weighing unit 114 and a percent moisture calculator 116. The analyzer 108 also includes a memory circuit 98, a firmware program 100, a display 102, a percent fat calculator 120 and a buffer 122.

The meat product weighing unit 114 has means, such as a tray, for supporting a quantity of a wet preheated beef or pork product. The unit 114 also has means for initially determining the weight of the wet preheated beef or pork product and the weight of the beef or pork product after the product has been substantially dried by the heat source 112 as described supra. From the meat product weighing unit 114, the wet and dry weight of the meat product is applied to the percent moisture calculator 116. The calculator includes means for calculating the percent moisture of the beef or pork product from the wet and dry weight data supplied by the meat product weighing unit 114. From the percent moisture calculator 116, the weight data is applied to the percent fat calculator 120 via the memory circuit 98. The calculator 120 functions in combination with the firmware program 100© which solves a beef formula or a pork formula to provide the equivalent percent fat of the beef or pork product. The percent fat figure is received and displayed on the display 102 as shown in FIG. 10.

In FIG. 10, is also shown an optional buffer 122 that receives the percent fat of the beef or pork product. From the buffer 122, the percent fat is applied through an output connector 124 to a printer 126 where the data shown on the display 102 is printed to provide a permanent record. The printer 126 may be an integral element of the integrated percent moisture and fat analyzer 108, as shown in FIG. 10, or it may consists of an external printer (not shown) that is connected by means of a cable assembly.

While the invention has been described in complete detail and pictorially shown in the accompanying drawings it is not to be limited to such details, since many changes and modifications may be made in the invention without departing from the spirit and scope thereof. Hence, it is described to cover any and all modifications and forms which may come within the language and scope of the appended claims.

I claim:

1. A process for determining the percent fat of a beef or pork meat product, wherein said process consists essentially of the following steps:

a) determine the percent moisture of said meat product by performing the following steps,
   (1) weigh a sample of a preheated said meat product to obtain the wet weight of said meat product,
   (2) subject said preheated meat product to a heat source until said meat product is substantially dry,
   (3) remove said meat product from the heat source and reweigh to obtain the dry weight of said meat product, and
   (4) calculate the percent moisture of said meat product by solving the following equation:

$$\text{percent moisture} = \frac{\text{wet weight} - \text{dry weight}}{\text{wet weight}} \times 100$$

b) enter said percent moisture into an integrated calculating device, consisting essentially of:
   (1) a keypad having a "B" key for calculating the percent fat of a beef product, a "P" key for calculating the percent fat of a pork product and ten keys 0–9 for entering the percent moisture of either the beef or pork product,
   (2) a microcontroller connected to said keypad and having:
      (a) a register or memory circuit means for receiving and storing the percent moisture figure of the beef or pork product as entered into the ten keys on said keypad,
      (b) a firmware program 100© having means for solving a beef formula and a pork formula when either the "B" key or "P" key on said keypad is depressed, wherein the equivalent percent fat of the selected meat product is determined,
   (3) a display having means for receiving the output from said microcontroller, and c) read on said device the percent fat equivalent to the entered said percent moisture.

2. The device as specified in claim 1 wherein said beef and pork formulas are as follows:

a) percent fat of $$\text{beef} = \frac{77.4 - \text{percent moisture of beef}}{0.786}$$

$$\text{pork} = \frac{78.4 - \text{percent moisture of pork}}{0.787}.$$

* * * * *